April 5, 1966
M. J. SLAYMAN
Plant Pat. 2,618
POMEGRANATE TREE
Filed Dec. 14, 1964
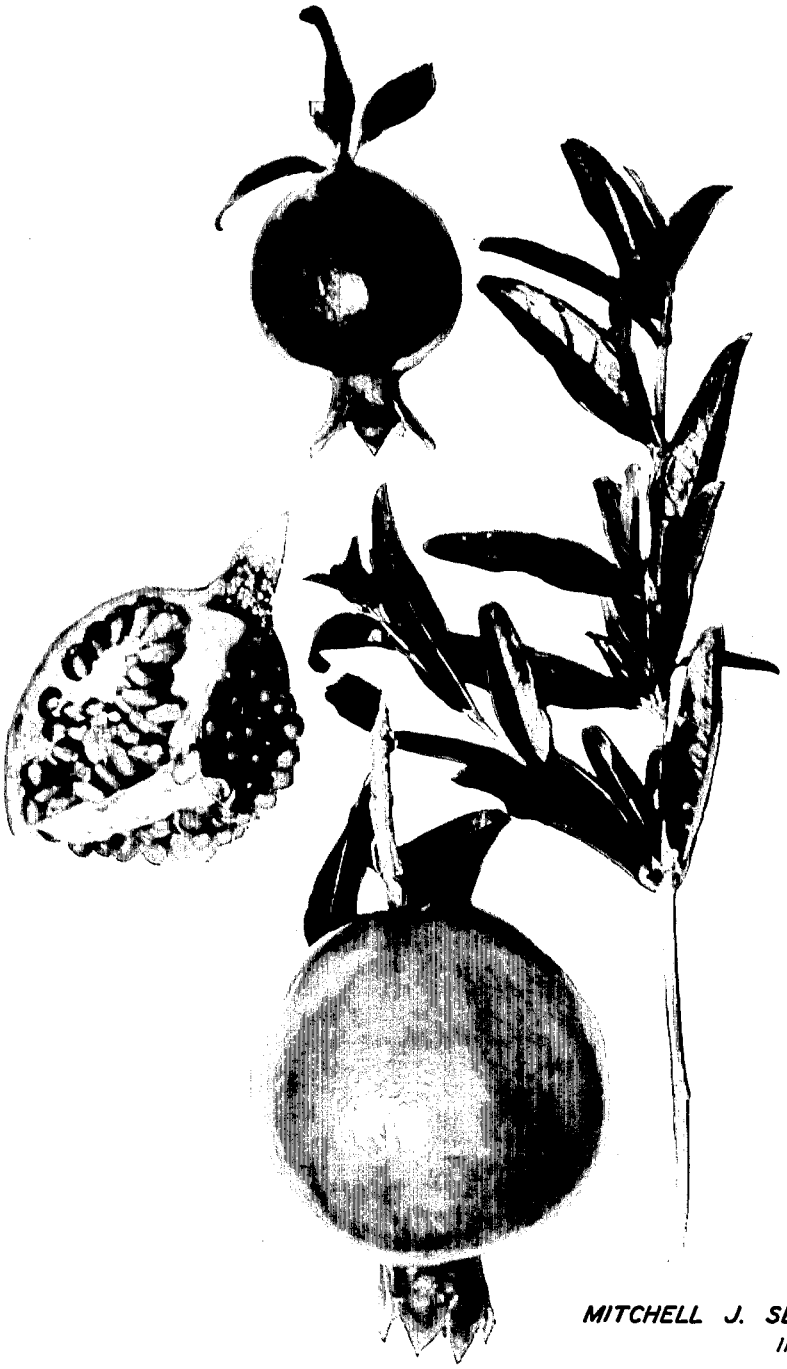
MITCHELL J. SLAYMAN
INVENTOR
Huebner & Worrel
ATTORNEYS United States Patent Office Plant Pat. 2,618
Patented Apr. 5, 1966

2,618
POMEGRANATE TREE

Mitchell J. Slayman, P.O. Box 1235, Lindsay, Calif.

Filed Dec. 14, 1964, Ser. No. 419,290
1 Claim. (Cl. Plt.—33)

The present invention relates to a pomegranate tree and more particularly to a new and distinct variety thereof broadly characterized by regular bearing of early ripening fruit of a deep red color and having a mildly acid pulp enclosing the seeds thereof.

The instant variety blooms approximately coincidentally with the Wonderful (unpatented) pomegranate tree. The fruit ripens about a month earlier than that of the Wonderful variety, and is of a slightly smaller size and of a deeper red color. In further comparison, the pulp enclosing the seed is less tart and has a mildly acid taste.

I discovered the present variety of pomegranate tree as a sport of the Wonderful variety growing on my grove at 1099 Parkside, Lindsay, California, located in the San Joaquin Valley. The sport was growing among other pomegranate trees exhibiting the normal characteristics of the Wonderful variety. The tree of the new variety very nearly resembles the Wonderful, and, except for the distinct color of the blossoms and fruit, the early ripening of the fruit, and the unique color contrast while in the green, or unripened stage, is substantially identical to the Wonderful.

The sport tree was not recognized as such until its first bearing season in 1960. At that time, the fruit was noted in the green stage as having a crown of deep red color, while the remaining body portion was of the typical pomegranate green coloration. The red color of the crown was substantially the same as the later acquired ripened color of the remaining body portion of the fruit. This crown of deep red color remained substantially constant during the green stage, even though the body portion of the fruit remained green until ripening took place.

The fruit ripened approximately one month earlier than other Wonderful pomegranate trees growing in the immediately adjacent area in the San Joaquin Valley area and was of a noticeably deeper red color. The pulp was of about the same color and appearance as that of the Wonderful, but was noted as having a less tart taste. The shape of the fruit was similar to the Wonderful, but slightly smaller in size.

In early 1961, cuttings were rooted from the recognized sport on my grove at 1099 Parkside, Lindsay, and developed into trees. These trees were of an appearance substantially identical to the parent tree, as well as other trees of the Wonderful variety. The trees developed from such cuttings first blossomed and bore fruit in 1964. The blossoms were observed to be of a darker red color than that of the Wonderful variety. During the green stage of the fruit, the distinctive red crown was noted to be substantially the same as that borne by the sport. The fruit ripened at about mid-August, as did that of the sport. The deeper red color and all other characteristics of the sport were identically reproduced in the trees developed from the cuttings.

The accompanying drawing is a color photograph of a characteristic twig of the subject pomegranate tree bearing foliage and a mature fruit. A fragment of an opened ripened pomegranate fruit is also shown, as well as a partially-ripened green fruit.

Referring more specifically to the pomological details of this new and distinct variety of pomegranate tree, the following has been observed under the climatic conditions prevailing at my grove in the San Joaquin Valley near Lindsay, California, and is a brief outline description thereof. All major color print identifications are by reference to Maerz and Paul Dictionary of Color.

*Tree*

With respect to size, branches, and leaves, the new variety of pomegranate tree is substantially identical to the Wonderful variety from which it is a sport.

Flowers: Blooms approximately coincidentally with the Wonderful variety; of about the same size, but of a darker red color (7–E–6).

*Fruit*

Size: Slightly smaller in size than that of the Wonderful variety.

Form: Typical of pomegranate tree fruit; a semi-globular body having characteristic pomegranate crown.

Skin:

*Color when green.*—Body of fruit is medium to light green, while the crown is a deep blood red to purplish red (5–L–6 to 7–E–6). Crown portion of new variety maintains this color throughout green and ripening stages, and assumes substantially same color as body portion when ripe. Body of fruit is mottled green and dark red as ripening progresses, as shown in the drawing.

*Color when ripe.*—Deep blood red to purplish red (5–L–6 to 7–E–6).

Pulp: Slightly less tart than Wonderful variety and has a mildly acid taste.

Maturity date: Ripens approximately one month earlier than Wonderful. State of California Department of Agriculture requires that all pomegranates for market contain no more than 1.85% acid. The normal pomegranate season in the San Joaquin Valley begins approximately about the middle of September, at which time the most mature fruit on trees of the Wonderful variety will have less than 1.85% acid. The fruit of the new pomegranate variety ripens about the middle of August, at which time the acid content has been tested between about 1.4% and 1.6%.

Although the new variety of pomegranate tree possesses the described characteristics under the growing conditions in Tulare County located in the southeastern portion of the San Joaquin Valley, it is to be understood that variation of the usual magnitude in characteristics incident to the growing conditions, fertilization, pruning and pest control is to be expected.

Having thus described and illustrated my new variety of pomegranate tree, what is claimed as new and desired to be secured by Letters Patent is:

A new and distinct variety of pomegranate tree substantially as illustrated and described and which is characterized by blooming at about the same time as the Wonderful (unpatented) pomegranate which it very nearly resembles in tree growth and appearance, but from which it is distinguished by the deeper red color of its blossoms and its regular bearing of fruit which displays a red crown while in a green stage, ripens about one month earlier than the Wonderful, is of a darker red color, and is slightly less tart in flavor.

No references cited.

ABRAHAM G. STONE, *Primary Examiner.*